(12) United States Patent
Halbert et al.

(10) Patent No.: US 8,361,031 B2
(45) Date of Patent: Jan. 29, 2013

(54) EXCHANGING INFORMATION BETWEEN DEVICES IN A MEDICAL ENVIRONMENT

(75) Inventors: Donald Halbert, San Diego, CA (US); Sreelal Chandrasenan, San Diego, CA (US); Daniel Vik, La Jolla, CA (US); Gregory Borges, San Diego, CA (US)

(73) Assignee: Carefusion 303, Inc., San Diego, CA (US)

( * ) Notice: Subject to any disclaimer, the term of this patent is extended or adjusted under 35 U.S.C. 154(b) by 0 days.

(21) Appl. No.: 13/015,391

(22) Filed: Jan. 27, 2011

(65) Prior Publication Data

US 2012/0197196 A1    Aug. 2, 2012

(51) Int. Cl.
*A61M 1/00* (2006.01)

(52) U.S. Cl. .................................................... 604/151

(58) Field of Classification Search ............... 604/890.1, 604/65–67, 131–147, 151; 128/DIG. 12, 128/DIG. 13
See application file for complete search history.

(56) References Cited

U.S. PATENT DOCUMENTS

| | | | |
|---|---|---|---|
| 6,359,612 B1 | 3/2002 | Peter | |
| 6,558,320 B1 * | 5/2003 | Causey et al. | 600/300 |
| 6,985,870 B2 * | 1/2006 | Martucci et al. | 705/3 |
| 7,092,796 B2 * | 8/2006 | Vanderveen | 700/282 |
| 7,231,263 B2 * | 6/2007 | Choi | 700/17 |
| 7,356,382 B2 * | 4/2008 | Vanderveen | 700/282 |
| 7,384,410 B2 * | 6/2008 | Eggers et al. | 604/67 |
| 2007/0296696 A1 | 12/2007 | Nurmi | |
| 2008/0114226 A1 | 5/2008 | Music et al. | |
| 2010/0001838 A1 | 1/2010 | Miodownik et al. | |
| 2010/0287006 A1 | 11/2010 | Cannon et al. | |

FOREIGN PATENT DOCUMENTS

| | | |
|---|---|---|
| EP | 1643401 | 4/2006 |
| KR | 1020090073042 | 7/2009 |
| WO | WO-2006/087689 | 8/2006 |

OTHER PUBLICATIONS

ISA/KR, International Search Report and Written Opinion for International Application No. PCT/US2012/022803, 12 pages, Jun. 1, 2012.
ISA/KR, International Search Report and Written Opinion for International Application No. PCT/US2012/022804, 7 pages, Jul. 30, 2012.

* cited by examiner

*Primary Examiner* — Manuel Mendez
(74) *Attorney, Agent, or Firm* — Fred C. Hernandez; Mintz, Levin, Cohn, Ferris, Glovsky and Popeo, P.C.

(57) ABSTRACT

A medical device including an operation determiner for determining operations to be performed by the medical device in response to a gesture of the device with respect to the medical device, and an operation data accessor for accessing operation data for the operation performed by the medical device.

26 Claims, 5 Drawing Sheets

EXCHANGING INFORMATION BETWEEN DEVICES IN A MEDICAL ENVIRONMENT

CROSS-REFERENCE TO RELATED U.S. APPLICATIONS

This Application is related to U.S. patent application Ser. No. 13/015,515, entitled, "Associating Devices in a Medical Environment" by Halbert et al., with filing date Jan. 27, 2011, and assigned to the assignee of the present invention.

BACKGROUND

Typically, association of a medical device with another device requires multiple data entries and screen navigations by a user of the medical device (e.g., clinician). For example, sending a medication order from a device to a specific infusion pump requires multiple steps related to (1) association of the device to the medical device, and (2) initiating a transfer of medication orders.

Moreover, a clinician may have to navigate through multiple screens to trigger a specific activity on the medical device. For example, if a clinician wants to view the last medication administration time on a device, the clinician selects multiple screens, screen controls and input data.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Embodiments of Associating a Medical Device and Another Device

Figure 1:
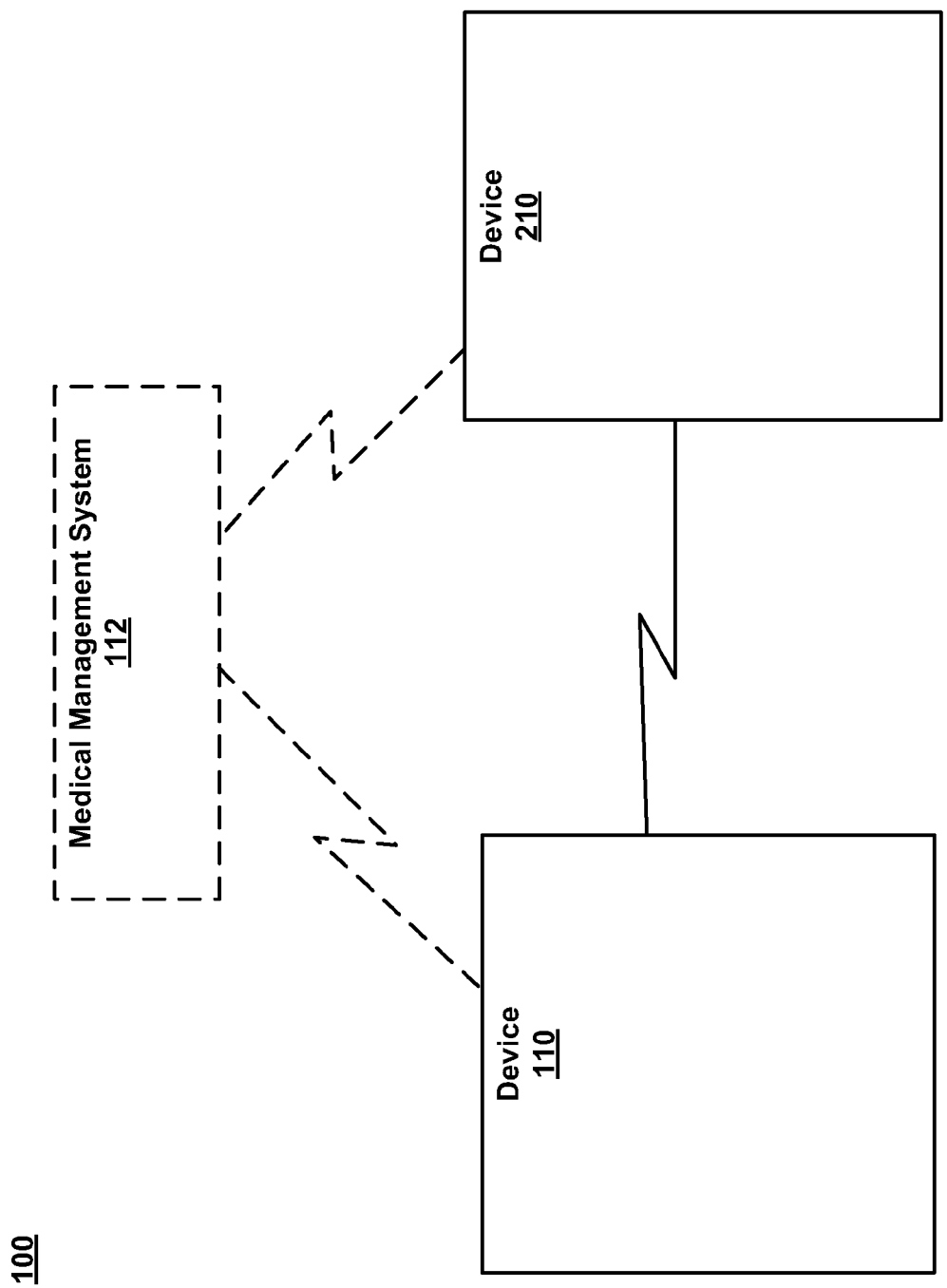
FIG. 1 illustrates an example of a medical environment, in accordance with an embodiment of the present invention.

FIG. 1 depicts an embodiment of medical system environment 100. Medical system environment 100 includes devices 110 and 210, and optionally medical management system 112. For example, devices 110 and 220 are able to wirelessly communicate with one another. Optionally, devices 110 and 220 are able to wirelessly communicate with medical management system 112.

In various embodiments, one of the devices 110 or 210 is a medical device (e.g., respirators, vital sign monitors, medication delivery systems, etc) and the other device is a mobile device (personal digital assistant (FDA), smart phone, cell phone, etc). Typically, (1) a medical device is any medical device that administers care to a patient, and (2) a mobile device is any mobile device that is able to be associated with the medical device and subsequently exchange information with the medical device to facilitate in the administration of care to the patient. In another embodiment, both devices 110 and 210 are medical devices. Moreover, the medical device and the mobile device include the capabilities to detect and communicate occurrences of gestures between the devices, which will be described in detail below.

When devices 110 and 210 are unassociated with one another, they are unable to exchange information with one another. However, once associated, devices 110 and 210 are able to exchange information with one another. Accordingly, devices 110 and 210 must be associated such that they properly and safely exchange information with one another, which will be described in detail below.

The following discussion will first describe the components and/or features of devices 110 and 210 in medical environment 100. Then the discussion will describe the functionality of the components and/or features during use of the devices in the medical environment. In particular, the discussion will describe the functionality of the components and/or features regarding the association of the medical devices.

Figure 2:
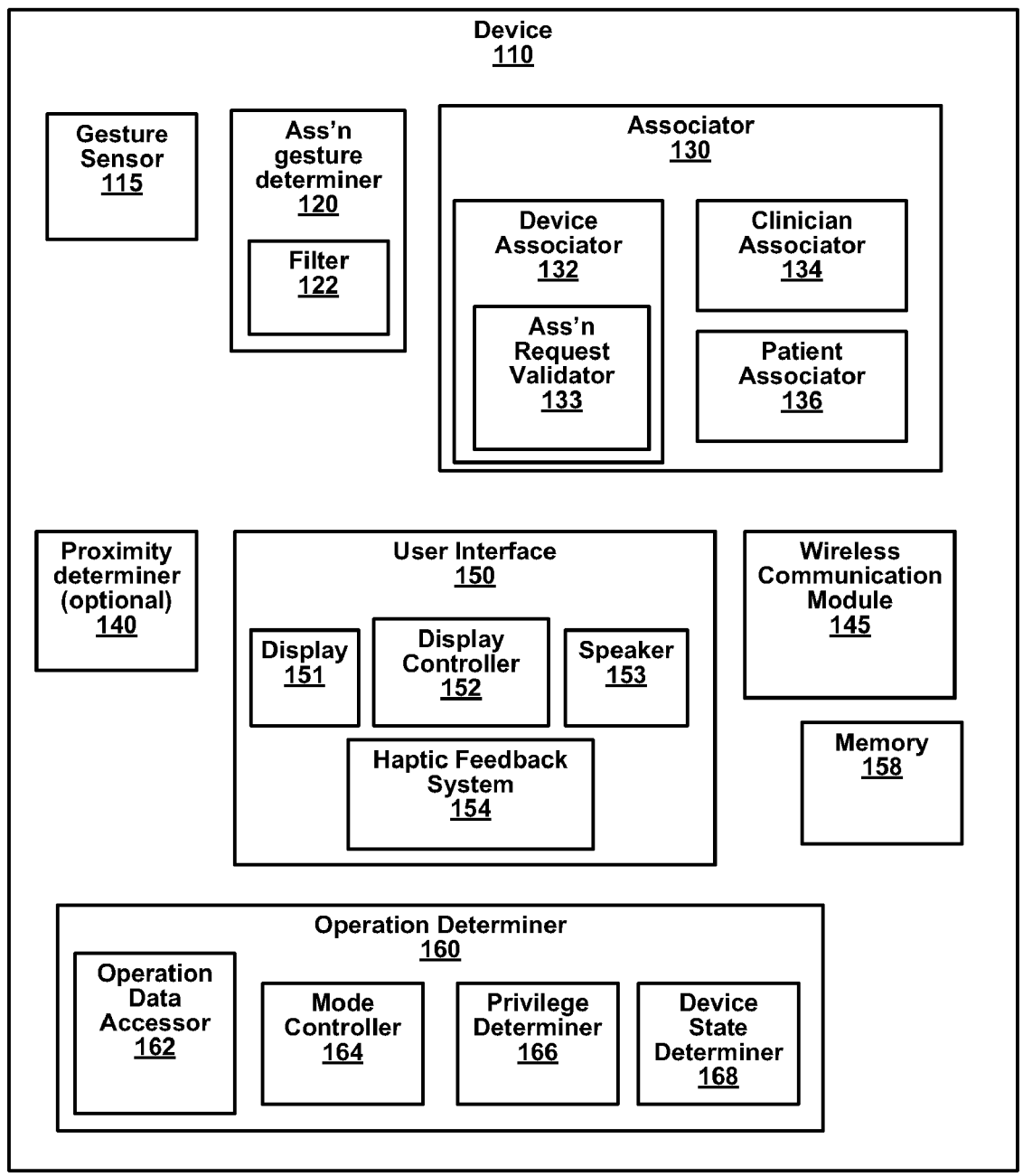
FIGS. 2 and 3 illustrate examples of devices, in accordance with embodiments of the present invention.

Referring to FIGS. 1 and 2, device 110 includes gesture sensor 115, association gesture determiner 120, associator 130, user interface 150, wireless communication module 145, memory 158, and optionally proximity determiner 140.

Gesture sensor 115 is for sensing or detecting a gesture of device 210 with respect to device 110. A gesture is a device movement and/or activity associated with the device for the intent of association of the device with another device. The gesture is detected within a short time window, such as a predefined short time window.

In various embodiments, gesture sensor 115 can be, but is not limited to, an accelerometer, gyroscope, etc. In one embodiment, gesture sensor 115 is an input sensor that senses a key press or a touch of a sensor. For example, if devices 110 and 210 do not have accelerometers or gyroscope, a user can generate a gesture by pressing a key on either or both devices within a short time window.

Association gesture determiner 120 is for determining that the gesture is an association gesture. An association gesture is a gesture initiating a request to associate devices 110 and 210, which will be described in further detail below.

Association gesture determiner 120 includes filter 122. Filter 122 is for filtering out unauthorized gestures or gestures which are not intended to initiate a request to associate devices 110 and 210.

Associator 130 includes device associator 132, clinician associator 134 and patient associator 136.

Device associator 132 is for associating/disassociating devices 110 and 210 based on the association gesture. Device associator 132 includes association request validator 133.

Association request validator 133 is for validating the association request (via the association gesture) based on information communicated between devices 110 and 210.

Clinician associator 134 is for associating/disassociating a clinician or device user with device 110. Patient associator 136 is for associating/disassociating a patient with device 110.

Proximity determiner 140 is for determining a proximity between devices 110 and 210. Proximity determiner 140 can detect proximity by utilizing RF signal strength, relative distance measurements using a global positioning system (GPS) or other location determining technologies.

Wireless communication module 145 is for wirelessly communicating information between devices 110 and 210, and optionally with medical management system 112. In various embodiments, the wireless communication is radio frequency (RF) communication (e.g., Bluetooth, WiFi, Zig-Bee, WiFi direct, etc).

Figure 3:
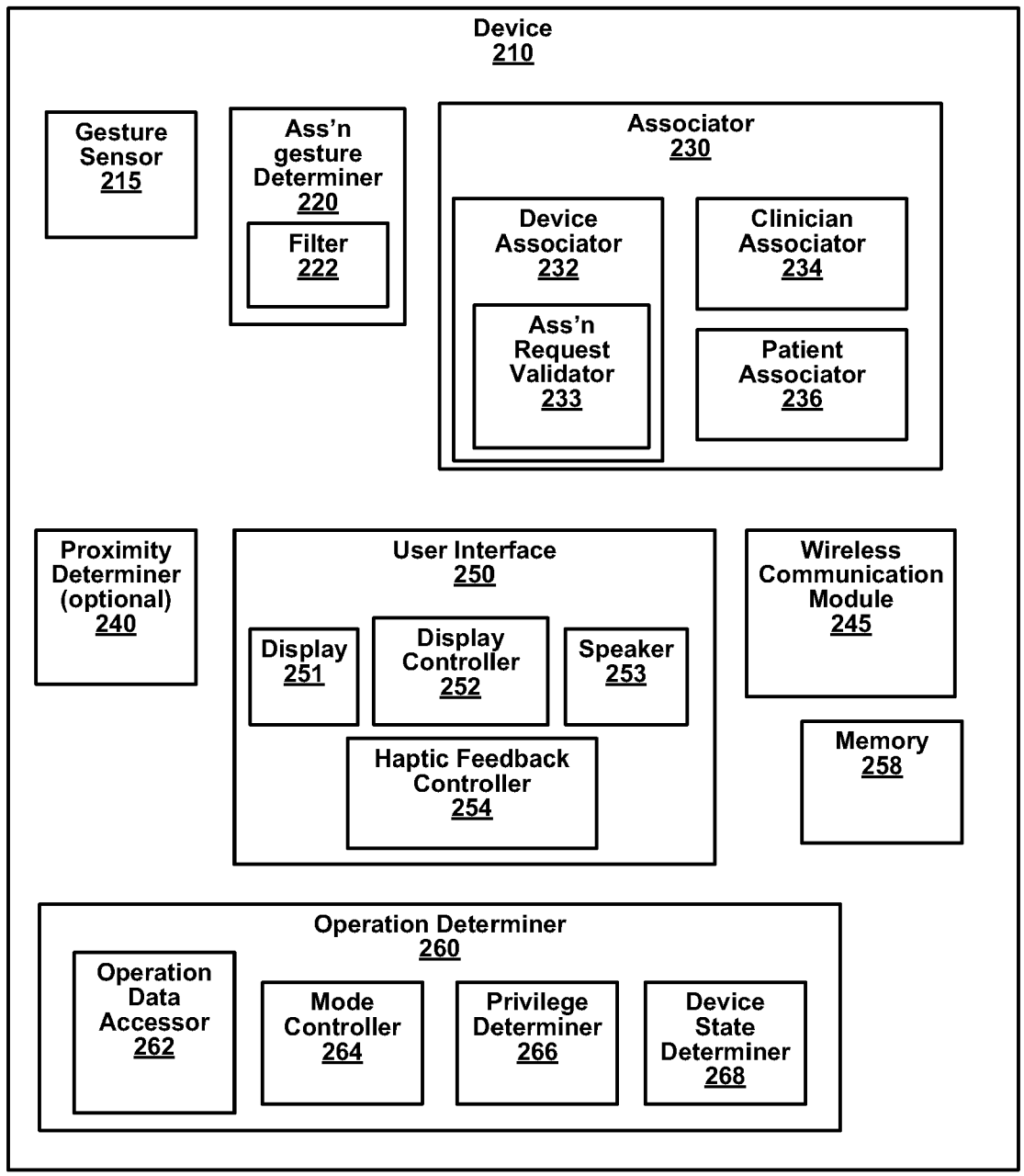

FIG. 3 depicts an embodiment of device 210. Similar to device 110, device 210 includes gesture sensor 215, association gesture determiner 220, associator 230, proximity determiner 240, user interface 250, wireless communication module 245 and memory 258.

The components included in device 210 are the same components and function similarly as the components of device 110. However, for brevity and clarity, the description herein will focus on the components of device 110.

As described above, devices 110 and 210 have to be associated with one another before they can communicate information with one another.

To request or initiate an association between devices 110 and 210, device 210 is moved to create a gesture with respect to device 110. For example, a clinician holding a PDA (e.g., device 210) taps or bumps the PDA on an infusion pump (e.g., device 110) to initiate an association between the PDA and the infusion pump.

In another example, just shaking the device or moving the mobile device in a specific pattern in a short time window can generate a gesture.

Detection of a request for association is achieved by physical contact with a characteristic acceleration and deceleration patterns on both devices. In other words, a gesture, can be, but is not limited to, a physical contact of device 210 with device 110, a pattern of a plurality of physical contacts of device 210 with device 110.

A gesture can be user input on one device (e.g., pressing a key) in concert with gesture on other device, or user inputs on both devices in concert (e.g., holding a push button, touching a touch screen, etc).

As such, gesture sensor 115 detects the acceleration and deceleration of the gestures. Likewise, gesture sensor 215 detects the corresponding acceleration characteristics of the gestures.

In various embodiments, gesture sensors 115 and 215 sense acceleration/deceleration patterns based on, among other things, (1) 3D motion in a similar trajectory based on weight of the devices, (2) maxima and minima acceleration within the time window, and/or (3) detection of spike patterns. It should be appreciated that acceleration/deceleration patterns sensed by gesture sensor 115 is opposite of the acceleration/deceleration patterns detected by gesture sensor 215. Additionally, gesture sensors 115 and 215 sense the acceleration/deceleration patterns within a small time window Association gesture determiner 120 determines whether or not the gestures detected by gesture sensors 115 and 215 are association gestures. In other words, some gestures may not be intended to associate the devices and are therefore not association gestures. Accordingly, the unintended gestures or unauthorized gestures are filtered out by filter 122. Moreover, the unauthorized gestures are logged in memory 158.

In one embodiment, association gesture determiner 120 determines whether or not the gesture is an association gesture based on predefined association gesture patterns. The predefined gesture patterns may be stored in memory 158, memory 258 and/or medical management system 112.

In another embodiment, association gesture determiner 120 determines whether or not the detected gesture is an association gesture based on gesture information received from device 210. For example, the gesture pattern detected at device 210 is compared with the gesture pattern detected at device 110. If the detected gestures correspond and are detected within the predefined time window (by both devices), then the detected gestures are deemed as association gestures. If the detected gestures do not correspond and are not detected within the predefined time window (by both devices), then the gestures are not deemed as association gestures and filtered out by filter 122.

In response to an association gesture, device associator 132 associates devices 110 and 210. In particular, association request validator 133 of device associator 132 validates the association request. For example, association request validator 133 validates the association request when an association gesture is detected, then mobile devices 110 and 210 exchange information based on the system state, device class, security policy and system configuration.

In response to an association gesture, clinician associator 134 associates a clinician with device 110. For example, a clinician who is logged into a FDA is associated to device 110, in response to clinician tapping the FDA on device 110. In particular, the gesture triggers a data transfer of clinician information from the mobile device to the medical device. The clinician information is then stored on the medical device and is used in clinical functions. A subsequent gesture may trigger a clinician log out and disassociation from the medical device.

In one embodiment, the clinician association is done when device 210 is ready to transfer clinician information and when device 110 is ready to accept clinician login.

It should be appreciated that it is desirable to be able to quickly associate a medical device with the clinician that is about to perform tasks and modify the care given by the medical device. Also, information about who performed specific tasks on a patient is embedded in clinical reports.

In response to an association gesture, patient associator 136 associates a patient with device 110. For example, in response to a clinician tapping a mobile device on a medical device, patient associator 136 associates the patient with the medical device. In another example, when multiple infusion pumps are used for administrating care to a patient, it is required to distribute the patient information such as, patient identification, patient weight, to the infusion pumps.

A medical device is often required to be configured for a specific patient, usually by using a patient identifier and/or patient name. The mobile device can streamline the configuration of the patient identifiers by allowing a clinician to transfer patient information from the mobile device by bumping the mobile device and the medical device.

In one embodiment, one of the devices does not include a gesture detector. As such, the detection of a request for association can be achieved by close proximity between the devices and acceleration/deceleration patterns detected on the device with the gesture detector.

For example, device 210 includes gesture sensor 215 and device 120 does not include gesture sensor 115. In this embodiment, gesture sensor 215 detects an association gesture and proximity determiner 240 searches for device 120 in close proximity to device 210. Device 210 also communicates an intent to associate with device 110.

User interface 150 communicates information to a user of device 110. Similarly, user interface 250 communicates information to a user of device 220. In general, display 151, speaker 153 and/or haptic feedback system 154 provide information to a user regarding the process of association between devices 110 and 210.

For example, display controller 152 controls the viewability of visual elements displayed on display 151. In such an example, information such as text and/or buttons change color when an association occurs.

In another example, speaker 153 makes a sound to indicate that an association gesture has occurred. Similarly, haptic feedback system 154 provides a tactile vibration to indicate that an association gesture has occurred.

Figure 4:
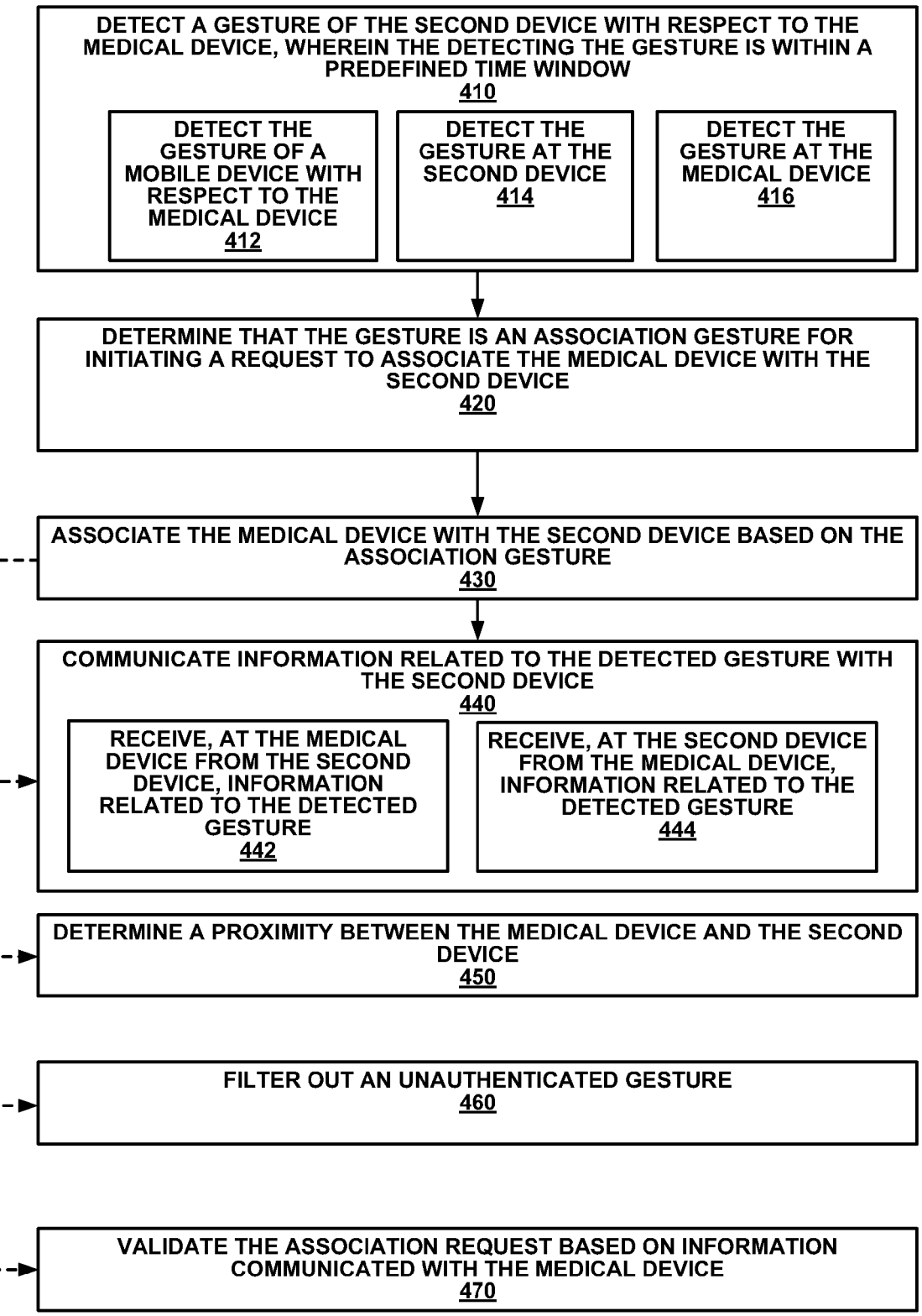
FIG. 4 illustrates an example of a method for associating a medical device with a second device, in accordance with an embodiment of the present invention.

FIG. 4 depicts an embodiment of a method 400 for associating a medical device with a second device. In various embodiments, method 400 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 400 is performed at least by device 110 and/or device 210, as described in FIGS. 1-3.

At 410 of method 400, a gesture of the second device with respect to the medical device is detected, wherein the detecting the gesture is within a predefined time window. For example, a taping of device 210 with respect to device 110 is detected by gesture sensor 115 within a predefined time window of 10 seconds.

In one embodiment, at 412, the gesture of a mobile device with respect to the medical device is detected. For example, the tapping of a PDA on an infusion pump to indicate a request for association between the FDA and the infusion pump is detected.

In another embodiment, at 414, the gesture is detected at the second device. For example, the tapping (e.g., a single or multiple taps) of the FDA on the infusion pump is detected by an accelerometer in the FDA.

In a further embodiment, at 416, the gesture is detected at the medical device. For example, the tapping of the FDA on the infusion pump is detected by an accelerometer in the infusion pump.

At 420, the gesture is determined to be an association gesture for initiating a request to associate the medical device with the second device. For example, association gesture determiner 120 determines that the tapping of the FDA on the infusion pump is a request to associate the FDA with the infusion pump.

At 430, the medical device is associated with the second device based on the association gesture. For example, an infusion pump is associated with another infusion pump based on an association gesture.

At 440, information related to the detected gesture is communicated with the second device. For example, information related to a gesture between a FDA and an infusion pump is exchanged between the FDA and the infusion pump.

In one embodiment, at 442, information related to the detected gesture is received at the medical device from the second device. For example, the acceleration pattern of the gesture detected at the FDA is wirelessly transmitted to the infusion pump.

In another embodiment at 444, information related to the detected gesture is received at the second device from the medical device. For example, the acceleration pattern of the gesture detected at the infusion pump is wirelessly transmitted to the FDA.

At 450, a proximity between the medical device and the second device is determined. For example, one of the devices does not include an accelerometer or gyroscope. As such, the detection of a request for association can be achieved by the proximity between the devices and acceleration/deceleration patterns detected on the device with the gesture detector.

At 460, an unauthenticated gesture is filtered out. For example, filter 122 filters out an unintended physical contact between a FDA and an infusion pump.

At 470, the association request based on information communicated with the medical device is validated. For example, association request validator 133 validates that an association request between a mobile device and medical device based, in part, that a mutual bump was detected.

Embodiments of Exchanging Data Between Devices

The discussion provided below will first describe the components and/or features of devices 110 and 210 in relation to the exchange of information. Then the discussion will describe the functionality of the components and/or features during use of the devices in the medical environment. In particular, the discussion will describe the functionality of the components and/or features regarding the exchanging of information between the devices to facilitate in operations performed by one or more of devices 110 and 210.

Referring now to FIGS. 1-3, device 110 further includes operation determiner 160. Operation determiner 160 includes operation data accessor 162, mode controller 164, privilege determiner 166 and device state determiner 168.

Operation determiner 160 is for determining operations or tasks to be performed in response to a gesture performed between devices 110 and 210. It should be appreciated that one gesture can result in multiple operations.

Operation data accessor 162 is for accessing operation data to facilitate in the operation to be performed by device 110. Mode controller 164 is for controlling a mode of device 110 based on the gesture. Privilege determiner 166 is for determining privileges of a clinician. Device state determiner 168 is for determining the device state of device 110.

Similar to device 110, device 210 includes operation determiner 260 operation data accessor 262, mode controller 264, privilege determiner 266, and device state determiner 268.

The components included in device 210 are the same components and function similarly as the components of device 110. However, for brevity and clarity, the description herein will focus on the components of device 110.

Devices 110 and 210 must be associated such that they properly and safely exchange information with one another. In general, after the association phase, devices 110 and 210 exchange information about the operations their respective states allow. The receiving side then performs zero or more of the allowed operations. There is no limitation in how many operations can be performed based on a single association gesture. The available operations can be based on what is currently displayed on the user interfaces, alarm state, device state, and physical or logical location, etc. Therefore, the exchanged information facilitates in the performing of operations by one or more of devices 110 and 210.

The information exchanged between the devices can facilitate in determining the operation to be performed by the devices. For example, devices 110 and 210 exchange information (via wireless communication modules 145 and 245) based on the system state, device class, security policy and system configuration. Accordingly, operation determiner 160 determines what operations are to be performed by device 110.

In general, the operations determined to be performed by the devices can include, but are not limited to, an operation performed in response to a gesture, an operation performed based on subsequent accessing of operation data, or an operation performed in response to bi-directional request of operation data between devices 110 and 210.

Moreover, the different types of operations are typically not authorized at all times. This depends on multiple factors, such what screen the clinician is viewing on the mobile device, and what state the medical device is in. Multiple operations may be performed in response to a single gesture. For example, transferring historical logs are done as a result of a single tap that also performs clinician login.

In particular, operation data accessor 162 can access operational data from device 210 to facilitate in the operations to be performed by device 110. Operation data accessor 162 can also access operational data stored on memory 158, memory 258 and/or medical management system 112. Moreover, operational data accessor 162 can access (e.g., receive, send) data via wireless communication module 145.

It should be appreciated that the information exchanged between the devices can occur before, during or after the performing of the operation. In one embodiment, operational information can be collected at run time from sensors on the medical device and transferred to the mobile device.

Various types of information related to the operations can be exchanged between the devices. Moreover, the exchanged information can be based on the system state, device class, security policy and system configuration.

The exchanged information can include, among other things, a transfer of data that forms an infusion order to the medical device from the mobile device; a transfer of historical logs from the medical device to the mobile device; a transfer of infusion status from the medical device to the mobile device; a transfer of device configuration from the mobile device to the medical device; a transfer of device configuration from the mobile device to the medical device; a transfer of calibration parameters from the mobile device to the medical device; a transfer of dataset profile, including care area, from the mobile device to the medical device; a transfer of data to wake up the medical device from a power save mode; a transfer of data to place the medical device into a power save mode; a transfer of data to silence an alarm on the medical device; and a transfer of configuration data, including software and firmware to perform device update (configuration update is for device synchronization and also applies to all device configuration changes).

It should be appreciated that the exchange of information can be in response to an association gesture between devices 110 and 210 and the state of the devices.

In particular, a mobile device can be used to collect and prepare information related to programming of a medical device. This can be an order transferred to the mobile device from a pharmacy system, an order created on the local user interface of the mobile device, or just programming parameters entered on the mobile device. Once an order or programming parameters are ready to be transferred to the medical device, the clinician can provide an association gesture (e.g., a bump) between the mobile device and the medical device and the transfer of the programming data is initiated. Once the programming data is transferred to the medical device, the operation of the program can be executed.

A mobile device can collect data from the medical device when an association gesture is detected. The collected data may include historical logs, system status, infusion status, clinical event logs, etc. The association gesture can also synchronize information such as patient status information.

The mobile device can be used to configure the medical device with drug data sets, calibration data, and configuration parameters. This data can be transferred when an association gesture is detected.

Privilege determiner 168 determines the privileges of the clinician that is logged into device 210 and associated to device 110. Accordingly, the operations to be performed and the information exchanged are dependent on the privileges of the user. For example, operation determiner 160 determines what operations are able to be performed based on the privileges of the user. Moreover, operation data accessor 162 accesses data based on the privileges of the user.

Device state determiner 168 determines the state of the devices. Accordingly, the operations to be performed and the information exchanged are dependent on the state of the devices. For example, operation determiner 160 determines what operations are able to be performed based on the state of either device or the aggregate state of the devices. Moreover, operation data accessor 162 accesses data based on the state of the devices.

It should be appreciated that a gesture can be used to wake up a medical device from a suspended mode (or state), or a sleep mode. A gesture can also put a device back into sleep mode or a power save mode. When the medical device is in an alarm state, a gesture with a mobile device silences the alarm.

Figure 5:
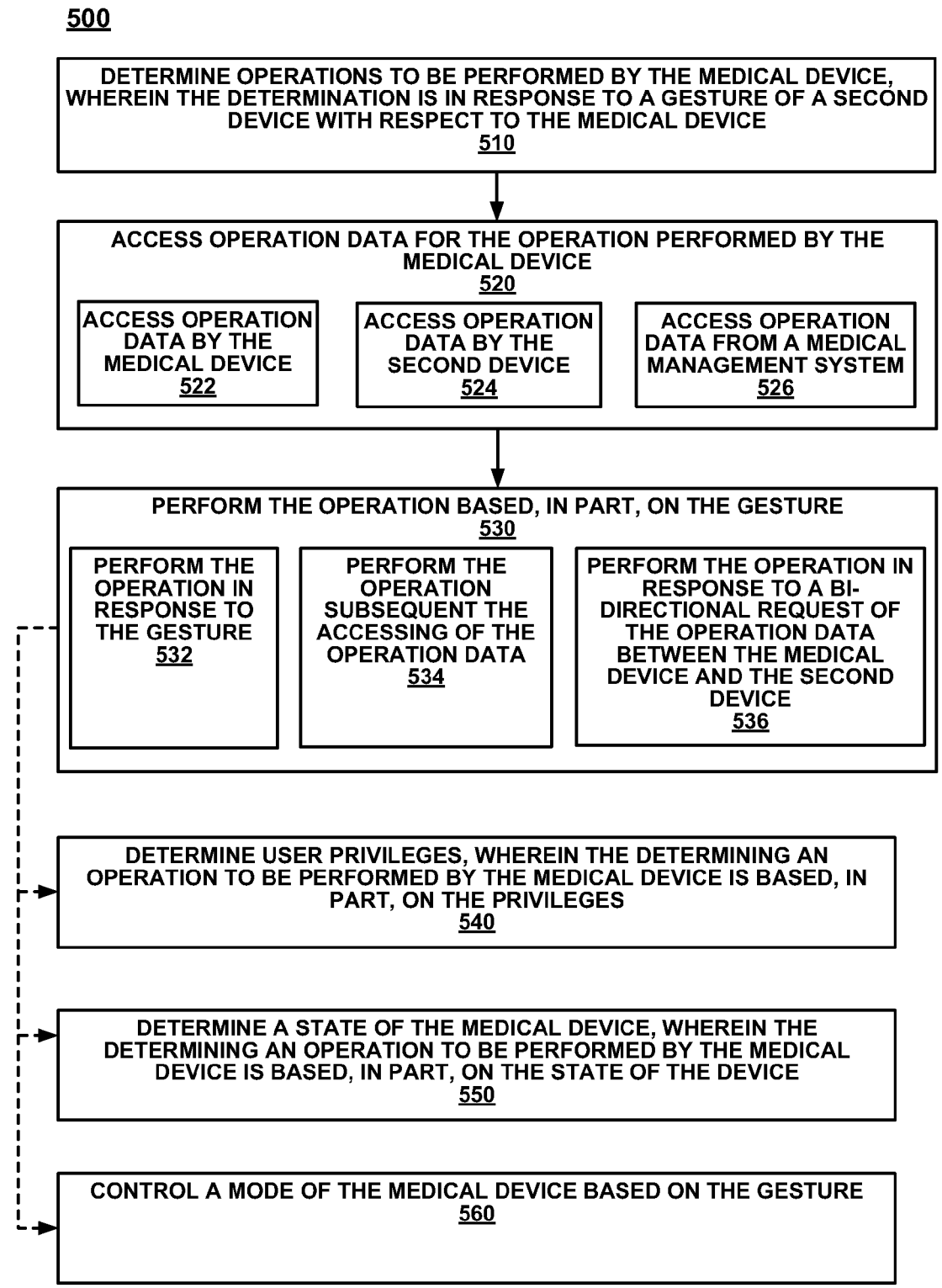
FIG. 5 illustrates an example of a method for performing an operation by a medical device, in accordance with an embodiment of the present invention.

FIG. 5 depicts an embodiment of a method 500 for performing an operation by a medical device. In various embodiments, method 500 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 500 is performed at least by device 110 and/or device 210, as described in FIGS. 1-3.

At 510, an operation is determined to be performed by the medical device, wherein the determination is in response to a gesture of a second device with respect to the medical device. For example, an infusion operation is determined to be performed by an infusion pump in response to a gesture of a PDA with respect to the infusion pump.

At 520, operation data is accessed for the operation performed by the medical device. For example, parameters for the infusion operation are transmitted to the medical device from the FDA.

In one embodiment, at 522, operation data is accessed by the medical device. For example, patient weight is transmitted by the medical device.

In another embodiment, at 524, operation data is accessed by the second device. For example, historical logs from the medical device are accessed by the mobile device.

In a further embodiment, at 526, operation data is accessed from a medical management system. For example, historical logs are transmitted from the medical management system to the mobile device and/or the medical device.

At 530, the operation performed is based, in part, on the gesture.

In one embodiment, at 532, the operation is performed in response to the gesture. For example, an operation of infusing medication to a patient is performed in response to tapping of the FDA onto the infusion pump.

In another embodiment, at 534, the operation is performed subsequent the accessing of the operation data. For example, the operation of infusing medication is performed after historical logs are transmitted to mobile device.

In a further embodiment, at 536, the operation is performed in response to a bi-directional request of the operation data between the medical device and the second device.

At 540, user privileges are determined, wherein the determining an operation to be performed by the medical device is based, in part, on the privileges. For example, the operation of infusing medication to a patient is based, in part, on the privilege of a doctor who is logged into the mobile device.

At 550, determine a state of the medical device, wherein the determining an operation to be performed by the medical device is based, in part, on the state of the device.

At 560, a mode of the medical device is controlled based on the gesture. For example, the mode of the medical device is changed from sleep mode to active mode in response to the gesture.

Various embodiments of the present invention are thus described. While the present invention has been described in particular embodiments, it should be appreciated that the present invention should not be construed as limited by such embodiments, but rather construed according to the following claims.

The invention claimed is:

1. A medical device comprising:
an operation determiner for determining operations to be performed by said medical device in response to a gesture of a second device with respect to said medical device, wherein said gesture is sensed by a gesture sensor selected from a group consisting of: an accelerometer and a gyroscope; and
an operation data accessor for accessing operation data for said operation performed by said medical device.

2. The medical device of claim 1, wherein said operation comprises:
an operation performed in response to said gesture.

3. The medical device of claim 1, wherein said operation comprises:
an operation performed based on subsequent accessing of said operation data.

4. The medical device of claim 1, wherein said operation comprises:
an operation performed in response to bi-directional request of said operation data between said medical device and said second device.

5. The medical device of claim 1, further comprising:
memory for storing said operation data.

6. The medical device of claim 1, further comprising:
a mode controller for controlling a mode of said medical device based on said gesture.

7. The medical device of claim 1, further comprising:
a privilege determiner for determining privileges of a user.

8. The medical device of claim 1, wherein said operation determiner further comprising:
a device state determiner for determining a state of said medical device, wherein said determining said operation to be performed by said medical device is based, in part, on said state of said medical device.

9. A mobile device comprising:
an operation determiner for determining an operation to be performed by a medical device in response to a gesture of said mobile device with respect to said medical device, wherein said gesture is sensed by a gesture sensor selected from a group consisting of: an accelerometer and a gyroscope; and
an operation data accessor for accessing operation data for said operation performed by said medical device.

10. The mobile device of claim 9, wherein said operation comprises:
an operation performed in response to said gesture.

11. The mobile device of claim 9, wherein said operation comprises:
an operation performed based on subsequent accessing of said operation data.

12. The mobile device of claim 9, wherein said operation comprises:
an operation performed in response to bi-directional request of said operation data between said medical device and a second device.

13. The mobile device of claim 9, further comprising:
memory for storing said operation data.

14. The mobile device of claim 9, further comprising:
a mode controller for controlling a mode of said medical device based on said gesture.

15. The mobile device of claim 9, further comprising:
a privilege determiner for determining privileges of a user.

16. The mobile device of claim 9, wherein said operation determiner further comprising:
a device state determiner for determining a state of said medical device, wherein said determining said operation to be performed by said medical device is based, in part, on said state of said medical device.

17. A method for performing an operation by a medical device, said method comprising:
determining an operation to be performed by said medical device, wherein said determination is in response to a gesture of a second device with respect to said medical device, wherein said gesture is sensed by a gesture sensor selected from a group consisting of: an accelerometer and a gyroscope;
accessing operation data for said operation performed by said medical device; and
performing said operation based, in part, on said gesture.

18. The method of claim 17, wherein said accessing operation data for operation performed by said medical device comprises:
accessing operation data by said medical device.

19. The method of claim 17, wherein said accessing operation data for operation performed by said medical device comprises:
accessing operation data by said second device.

20. The method of claim 17, wherein said accessing operation data for operation performed by said medical device comprises:
accessing operation data from a medical management system.

21. The method of claim 17, wherein said performing said operation based, in part, on said gesture comprising:
performing said operation in response to said gesture.

22. The method of claim 17, wherein said performing said operation based, in part, on said gesture comprising:
performing said operation subsequent said accessing of said operation data.

23. The method of claim 17, wherein said performing said operation based, in part, on said gesture comprising:
performing said operation in response to a bi-directional request of said operation data between said medical device and said second device.

24. The method of claim 17, further comprising:
determining user privileges, wherein said determining an operation to be performed by said medical device is based, in part, on said privileges.

25. The method of claim 17, further comprising:
determining a state of said medical device, wherein said determining an operation to be performed by said medical device is based, in part, on said state of said device.

26. The method of claim 17, further comprising:
controlling a mode of said medical device based on said gesture.

* * * * *

UNITED STATES PATENT AND TRADEMARK OFFICE
CERTIFICATE OF CORRECTION

| | | |
|---|---|---|
| PATENT NO. | : 8,361,031 B2 | Page 1 of 1 |
| APPLICATION NO. | : 13/015391 | |
| DATED | : January 29, 2013 | |
| INVENTOR(S) | : Donald Halbert et al. | |

It is certified that error appears in the above-identified patent and that said Letters Patent is hereby corrected as shown below:

Title page, item [57] Abstract, in the first line, "including" should read --includes--.

In the Specification

In Column 2, line 8, insert a --.-- after "etc".

In Column 3, line 58, insert a --.-- after "window".

In Column 2, line 9;
Column 4, line 25 and line 26;
Column 5, line 32, line 36, line 37, line 39, line 44, line 45, line 53, line 54, line 58, and line 63; and
Column 6, line 5, "FDA", each occurrence, should read --PDA--.

Signed and Sealed this
Third Day of September, 2013

Teresa Stanek Rea
*Acting Director of the United States Patent and Trademark Office*